United States Patent [19]

Welborn, Jr.

[11] Patent Number: 4,952,714

[45] Date of Patent: Aug. 28, 1990

[54] NON-AQUEOUS PROCESS FOR THE PREPARATION OF ALUMOXANES

[75] Inventor: Howard C. Welborn, Jr., Houston, Tex.

[73] Assignee: Exxon Chemical Patents Inc., Linden, N.J.

[21] Appl. No.: 391,222

[22] Filed: Aug. 8, 1989

Related U.S. Application Data

[63] Continuation-in-part of Ser. No. 210,881, Jun. 22, 1988, abandoned.

[51] Int. Cl.$^5$ ................................................ C07F 5/06
[52] U.S. Cl. .................................................... 556/179
[58] Field of Search ......................................... 556/179

[56] References Cited

U.S. PATENT DOCUMENTS 3,049,407  8/1962  Köster .................................. 556/179
4,665,208  5/1987  Welborn et al. ..................... 556/179

OTHER PUBLICATIONS

Ashby, "J.A.C.S.", 81, p. 4791 (1959).
Storr et al., "J.A.C.S.", 90, p. 3173 (1968).

Primary Examiner—Paul F. Shaver
Attorney, Agent, or Firm—M. B. Kurtzman

[57] ABSTRACT

A process for the preparation of hydrocarbylalumoxanes comprising oligomeric, linear and/or cyclic hydrocarbylalumoxanes which comprise contacting a hydrocarbylaluminum dissolved in an inert dry organic liquid with a trihydrocarbylboroxine. Preferably, the trihydrocarbylboroxine is prepared by the reaction of boron oxide with trihydrocarbylborane.

6 Claims, No Drawings

NON-AQUEOUS PROCESS FOR THE PREPARATION OF ALUMOXANES

This is a continuation-in-part of copending application Ser. No. 210,881, filed June 22, 1988, now abandoned.

FIELD OF THE INVENTION

The present invention relates to the non-aqueous preparation of alumoxanes, preferably trimethylalumoxane. The invention particularly relates to the use of trialkylboroxine in the preparation of alumoxanes.

BACKGROUND OF THE INVENTION

Alumoxanes are the products of partial hydrolysis of hydrocarbylaluminum compounds and have been found useful in a variety of chemical reactions, including catalyst components for polymerization catalysts and especially as a component for catalysts in the preparation of high-activity, homogeneous Ziegler catalysts, as is described, for example, in U.S. patent application 501,740, filed June 6, 1983.

Various processes are known for the preparation of alumoxanes, the simplest being to add water in predetermined amounts and under controlled conditions to a hydrocarbylaluminum compound as described in U.S. Pat. No. 3,242,099. Alumoxanes can also be obtained, for example, by the action of water vapor on a benzene solution of a trialkylaluminum (J. Am. Chem. Soc. 90, 3173 [1968]) by using lithium dialkylaluminates as the organoaluminum starting compound (J. Am. Chem. Soc., 89, 173 [1967]). Other known methods for preparing alumoxanes include oxidizing aluminum-hydrocarbon compounds with lead dioxide (J. Organomet. Chem., 43, 81 [1972]), treating an alkylaluminum with alkyldistannoxanes [($R_3Sn)_2O$] in place of water (Racanelli, P. and Porri, L., Europ. Polym. J., 6, 751 [1970]) and hydrolyzing alkylaluminums with copper sulfate containing water of crystallization as suggested in European patent application No. 0035242.

In Australian Patent No. 20861/83, Kaminsky, et al. discloses a method of preparing alumoxanes by contacting aluminum salts containing water of crystallization with a trialkylaluminum. It is taught that the alumoxanes are obtained in higher yields and greater purity.

In many of these processes, because of the highly exothermic nature of the reaction between the water and the hydrocarbylaluminum, the reaction can easily get out of control or even become explosive. While the use of $CuSO_4.5H_2O$ as a source of water provides for the slow addition of water, thus reducing the risk of local excesses of water and thereby reducing the probability of a runaway or explosive reaction, the method suffers from some drawbacks. For example, the Cu(II) may be reduced to Cu(I) or even to metallic copper during the reaction with an alkylaluminum, such as trimethylaluminum. This can lead to the introduction of sulfate groups and other undesirable types of functionalities, as well as copper, into the alumoxane preparation. The alumoxane product, therefore, prior to use as a component of a catalyst system in a polymerization process, must be filtered, purified and recrystallized, since otherwise adverse conditions will exist during the polymerization, and the quality and quantity of the polymer will be adversely affected. Another disadvantage associated with $CuSO_4.5H_2O$ in preparation of alumoxane is the low yield which is on the order of about 30% relative to the aluminum trialkyl employed.

Some of these problems can be essentially eliminated, if one employs hydrated salts as the source of water in the preparation of alumoxanes, such as methyl alumoxane wherein the metal component is not reduced during the alumoxane preparation. Such a solution is disclosed in U.S. Pat. No. 4,665,208, issued to Welborn on May 12, 1987.

The disadvantage associated with using hydrated salts is that the heterogeneous solution of trialkylaluminum, hydrated salt and hydrocarbon still have the potential for a violent reaction during the formation of the alkylalumoxane even though the danger is greatly reduced. Consequently, there is still a need for a process which can safely and efficiently produce hydrocarbylalumoxanes.

Attempts to react boron oxide with trialkylaluminum without the intermediate step of producing trihydrocarbylboroxine have been unsuccessful. However, the reaction of boron oxide with trialkylboron to yield trialkylboroxine is disclosed in "The Reaction of Triorganoboranes with Boric Acid" by G. F. Hennion, et al., Journal of American Chemical Society, vol. 79, p. 5194 (1957). This reaction proceeds according to the following stoichiometry:

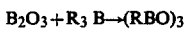
$$B_2O_3 + R_3B \rightarrow (RBO)_3$$

It has also been disclosed in "New Synthesis of Trialkylboranes," by G. C. Ashby, Journal of American Chemical Society, vol. 81, p. 4791 (1959), that trialkylboroxine produced in the above reaction can be reacted with trialkylaluminum to yield alumina and trialkylborane according to the following stoichiometry:

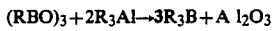
$$(RBO)_3 + 2R_3Al \rightarrow 3R_3B + Al_2O_3$$

In a similar reaction scheme published by J. G. Ruff entitled "A New Preparation of Some Dimethylalumino Derivations of Boron," Journal of Organic Chemistry, vol. 27, p. 1020 (1962), alkylboroxine was reacted with trisdimethylaluminoalane to yield a by-product generally identified as $[(CH_3)_2NAlO^-]_x$. The stoichiometry of this reaction was described as follows:

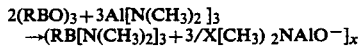
$$2(RBO)_3 + 3Al[N(CH_3)_2]_3 \rightarrow (RB[N(CH_3)_2]_3 + 3/X[CH_3)_2NAlO^-]_x$$

Similarly, Koster U.S. Pat. No. 3,049,407 teaches a process for synthesizing boron alkyls and highly active aluminum oxide. The synthesis consists of reacting an aluminum trialkyl and boroxol system first at a temperature below 100° C. and then at a temperature of between 150° C. and 220° C. The first stage reaction proceeds as

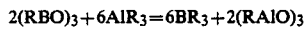
$$2(RBO)_3 + 6AlR_3 = 6BR_3 + 2(RAlO)_3$$

This is followed directly and without disturbing system concentrations by the second stage which can be described as

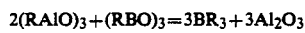
$$2(RAlO)_3 + (RBO)_3 = 3BR_3 + 3Al_2O_3$$

The overall process yielding the boron alkyl and aluminum oxide is the combination of the two reaction steps or

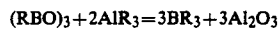
$$(RBO)_3 + 2AlR_3 = 3BR_3 + 3Al_2O_3$$

However, none of these references mentions that a mixture of linear and/or cyclic alkylalumoxanes can be safely and efficiently produced from trihydrocarbyl-boroxine and trialkylaluminum.

SUMMARY OF THE INVENTION

The alumoxanes which are prepared in accordance with this invention are oligomeric, linear and/or cyclic hydrocarbylalumoxanes represented by the formulae:

$$R-(Al-O)_n-AlR_2 \quad\quad (I)$$
$$\quad\quad\quad |$$
$$\quad\quad\quad R$$

for oligomeric, linear alumoxanes and $$(-Al-O-)_m \quad\quad (II)$$
$$\quad |$$
$$\quad R$$

for oligomeric, cyclic alumoxanes, wherein "n" is 1-40, preferably 4-40, "m" is 3-40, preferably 4-40, and R is a $C_1-C_8$ alkyl group and preferably methyl. It is generally known that the alumoxanes will evidence desirable activity when "m" and "n" are greater than 4 and R is methyl.

In the preferred embodiment, the general procedure in accordance with this invention is to first form the hydrocarbon soluble liquid trihydrocarbylboroxine, $(RBO)_3$. This can be accomplished by combining boron oxide with trihydrocarbylborane according to the following stoichiometry:

$$B_2O_3 = R'_3B \rightarrow (R'BO)_3 \quad\quad (III)$$

wherein R' can be a $C_1=C_{10}$ alkyl group or a $C_6===C_{10}$ aryl group, desirably a $C_1=C_{10}$ alkyl group and preferably R' is methyl or ethyl. Next, trihydrocarbylboroxine is combined with trialkylaluminum to form an alkylalumoxane and trihydrocarbylborane believed to be according to the following stoichiometry:
$(n+m)(RBO)_3+3(n+m+1)\quad R_3\quad Al \rightarrow 3-(RAlO)_m+3[R=(R=Al=O)_n=AlR_2]+3(m+n)R_3B$
wherein the sum (m+n) is 4-80, preferably 8-80, and most preferably 10-60. The R groups of the trialkylboroxine and the trialkylaluminum can be the same or different, most preferably all R groups are the same. If the R groups are different, a mixture of alkylalumoxane containing a mixture of R group is produced.

Since trihydrocarbylboroxine is soluble in the hydrocarbon solution, it permits a homogeneous reaction to occur with the trialkylaluminum, resulting in better control of the reaction stoichiometry and product properties, e.g., degree of oligomerization.

Illustrative of the hydrocarbylboroxines which can be employed are trimethylboroxine, triethylboroxine, tri-n-butylboroxine, triphenylboroxine, and unsymmetrical boroxines such as dimethylethylboroxine and the like.

DETAILED DESCRIPTION OF THE INVENTION

The present invention is directed toward a method for preparing alumoxanes, preferably methylalumoxanes, useful as one of the components in the active catalyst complex for the polymerization of olefins and particularly ethylene to high molecular weight polyethylenes, such as Linear Low Density Polyethylene (LLDPE) and High Density Polyethylene (HDPE). The polymers are intended for fabrication into articles by extrusion, injection molding, thermal forming, rotational molding and the like. In particular, the polymer prepared with the catalyst complex are homopolymers of ethylene and copolymers of ethylene with higher α-olefins having from 3 to about 10 carbon atoms and preferably 4 to 8 carbon atoms. Illustrative of the higher α-olefins are butene-1, hexene-1 and octene-1. Illustrative of the alkylaluminum compounds which can be employed are trimethylaluminum, triethylaluminum, dimethylaluminum chloride, and diethylaluminum chloride, and the like. Trimethylaluminum is preferred.

The active catalyst complex useful in polymerization comprises a metallocene and an alumoxane which can be adsorbed onto the surface of a support material. Alumoxanes are oligomeric aluminum compounds represented by the general formula: $(R-Al-O)_m$, a cyclic compound and $R(R-Al-O-)_nAlR_2$, which is a linear compound. In the general formula, "R" is a $C_1-C_{10}$ alkyl group, such as methyl, ethyl, propyl, butyl, isobutyl and pentyl, and "n" is an integer from 1 to about 40 and "m" is an integer from 3 to 40, and they represent the degree of oligomerization of the alumoxane. Preferably, "R" is methyl, and "n" is 4-40, and "m" is 4-40. Generally, in the preparation of alumoxanes from the reaction of trimethylaluminum and water, a mixture of linear and cyclic compounds is obtained. Generally, an alumoxane having a degree of oligomerization greater than 4 will, for a given metallocene, produce a catalyst complex of higher activity than will an alumoxane having a lower degree of oligomerization less than 4. The procedure by which alumoxane is produced will affect the degree of oligomerization of the alumoxane.

The metallocene useful as the other component of the catalyst complex may be any of the organometallic coordination compounds obtained as a cyclopentadienyl derivative of a transition metal. Metallocenes which are useful for preparing an active catalytic complex are the mono-, bi-, and tri-cyclopentadienyl or substituted cyclopentadienyl metal compounds and most preferably, bicyclopentadienyl compounds. Of the metallocenes, zirconocenes and titanocenes are most preferred. A person skilled in the art can readily determine the appropriate metallocene and the relative mole ratios needed to make an effective active catalyst.

Heretofore, the alumoxane component of the active catalyst complex has been prepared by contacting water in the form of a moist solvent with a solution of alkylaluminum in a suitable organic solvent such as benzene, toluene or an aliphatic hydrocarbon. As noted earlier, this procedure is susceptible to fire and explosion hazards which require the use of explosion-proof equipment and carefully controlled reaction conditions. In an alternative method, heretofore employed for the separation production of alumoxane, an alkylaluminum is contacted with a hydrated salt, such as hydrated copper sulfate. The method comprises treating a dilute solution of alkylaluminum in toluene with a copper sulfate pentahydrate. A slow, controlled hydrolysis of the alkylaluminum to alumoxane results which substantially eliminates the fire and explosion hazard, but with a disadvantage of the creation of hazardous waste products that must be disposed of and from which the alumoxane must be separated before it is suitable for use in the production of an active catalyst complex.

In accordance with the preferred embodiment of the present invention, the alumoxane complex is prepared by reacting boron oxide with trihydrocarbylborane to form trihydrocarbylboroxine. Next, trihydrocarbylboroxine is combined with trialkylaluminum to form an alkylalumoxane and trihydrocarbylborane.

By first forming the hydrocarbon soluble liquid trihydrocarbylboroxine, a homogeneous reaction can occur with the trialkylaluminum resulting in better control of the reaction stoichiometry and product properties, such as the degree of oligomerization. Since the reaction takes place in a homogeneous solution, there is less potential for the reaction to proceed violently, unlike heterogeneous mixtures of water, trimethylaluminum and hydrocarbon or mixtures of hydrated salt, trimethylaluminum and hydrocarbon. A further advantage is that a gaseous product, such as methane gas, is not produced during reaction. Therefore, there is no need for constant venting which has the potential for overpressurization and loss of reactants through venting.

In addition, the boroxine is readily produced using an inexpensive and readily available compound, boron oxide ($B_2O_3$) and a boric acid derivative. The reaction of the boroxine and alkylaluminum produces more borane than is used in the production of the boroxine and all by-product borane compounds can be hydrolyzed with water to produce harmless boric acid which can be readily disposed of, converted to boron oxide or recovered by, for example, distillation.

The ratio by volume between the inert solvent and the hyrdrocarbylaluminum employed should be from about 4:1 to about 25:1 or greater, and preferably about 8:1. The molar ratio of boron oxide to hydrocarbylborane can be from about 2:1 to about 1:2, and preferably about 1:1 to produce hydrocarbylboroxine. The molar ratio of trihydrocarbylboroxine to hydrocarbylaluminum should be from about 1:3.05 to about 1:4, and preferably about 1:3.3. Ratios of hydrocarbylaluminum greater than about 4 can result in excess unreacted hydrocarbylaluminum being present in the reaction product. Excess, unreacted hydrocarbylaluminum generally will not affect the usefulness of the product hydrocarbylalumoxane. At ratios of hydrocarbylaluminum to hydrocarbylboroxine of less than 3, alumina can be formed. These ratios may not only depend on the stoichiometry of the chemical reaction but also upon factors which influence the equilibrium of the reaction, such as temperature. Generally, the temperature of the reactions should be between about 10° C. to about 80° C. The reaction between the hydrocarbylaluminum and the hydrocarbylboroxine must be carried out in an oxygen-free, inert atmosphere which can be at atmospheric, subatmospheric, or superatmospheric pressure. Preferably the reaction is carried out at atmospheric or slightly superatmospheric pressure (1-2 bar) under nitrogen.

Completion of the reaction between the boron oxide and the hydrocarbylborane is indicated by the cessation of hydrocarbylboroxine production. Generally, the reaction time will be between about 2 and about 72 hours, depending on the temperature of the reaction. The reaction time between hydrocarbylboroxine and hydrocarbylaluminum can be between about 0.1 and about 24 hours. Usually the reaction time will be between 0.5 hours and about 4 hours.

It is preferred that the hydrocarbylboroxine be added to the hydrocarbylaluminum. This order of mixing forces the hydrocarbylboroxine to undergo reaction in the context of a transient localized excess of hydrocarbylaluminum and a transient localized deficiency of the hydrocarbylboroxine. In order to obtain a safe reaction rate, the rate of addition of boroxine to hydrocarbylaluminum should not exceed about 0.2 moles per minute per liter of reaction medium.

The solvents employed in dissolving the hydrocarbylaluminum can be any of the known inert organic solvents, preferably aliphatic or aromatic solvents, such as toluene, benzene, hexane, heptane, iso-octane, cyclohexane, methylcyclohexane, decane, and the like, and preferably the same solvent is employed for dissolving the alkylaluminum and the boroxine. Toluene and heptane are preferred solvents.

While the invention is described in connection with the specific examples below, it is understood that these are only for illustrative purposes. Many alternative, modifications and variations will be apparent to those skilled in the art in light of the below examples and such alternatives, modifications and variations fall within the general scope of the claims.

EXAMPLES

Example 1 Preparation of Triethylboroxine

A 500 cc round bottom flask was equipped with water cooled reflux condenser an electrically heated mantle, and a nitrogen bubbler to maintain an inert atmosphere. To the flask under nitrogen was added 70.0 g of $B_2 O_3$ (Aldrich Gold Label) which had been ground to a powder in a mortar under dry nitrogen. Neat triethylborane (100.0 g) was added to the boron oxide all at one time and the reaction flask was set up for refluxing. Reflux was continued for 5 days at which point the reflux condenser was changed for a distillation condenser and the liquid was distilled in two fractions. The second fraction yielded 60 cc of a colorless liquid which distilled at 148° C. The H-1 and B-11 NMR of the second fraction indicated that it was pure triethylboroxine.

Example 2 Preparation of Methylalumoxane

A 100 cc round bottom flask was equipped for magnetic stirring in an inert, dry nitrogen atmosphere. Neat trimethylaluminum (2.37 g, 0.033 moles) was weighed into the flask followed by 43 g of distilled toluene. Into another flask was weighed 1.68 g of neat triethylboroxine (0.010 moles), followed by 43 g of distilled toluene. With stirring, the triethylboroxine solution was added to the trimethylaluminum solution in 5-10 cc increments separated by 5 minute intervals. The solution remained clear and colorless during and after the additions. The solution was capped and stored under nitrogen.

Example 3 Preparation of Methylalumoxane

A 100 cc round bottom flask was equipped for magnetic stirring in an inert, dry nitrogen atmosphere. Neat triethylboroxine (1.68 g, 0.033 moles) was weighed into the flask and 43 g of distilled toluene was added. Into another flask was weighed 2.37 g of triethylaluminum, followed by 43 g of distilled toluene. With stirring, the trimethylaluminum solution was added to the triethylboroxine solution in 5-10 cc increments separated by 5 minute intervals. The solution became cloudy after the first addition and a gelatinous solid separated from the solution. The solution containing the precipitated solid was capped and stored under nitrogen.

Example 4 L Polymerization Using Methylalumoxane

A 1-liter Zipperclave stainless steel reactor vessel equipped with an inclined blade stirrer, an external jacket for temperature control, a septum inlet and vent line, and a regulated supply of dry ethylene and nitrogen, was cleaned with boiling toluene and dried and deoxygenated with a nitrogen flow. The reactor temperature was adjusted to 80° C., and 400 cc of distilled toluene was added. Two milliliters of the final solution from Example 2 was injected by syringe, and the mixture was stirred at 0 psig under nitrogen. A toluene solution (0.10 cc) containing 0.10 mg of dissolved bis(n-butylcyclopentadienyl)zirconium dichloride was injected. Immediately 90 psig of ethylene was admitted and the reactor was stirred and maintained at 80° C. for 5 minutes at a constant pressure of 90 psig. The product was recovered by rapidly venting, cooling, and opening the reactor. Residual toluene was evaporated in a stream of air, and the yield was weighed. The product was determined to be 10.0 g of polyethylene by infrared and gel permeation chromatography. The catalyst activity was calculated to be 885,000 grams polymer per gram zirconium-hour-bar.

Example 5 Polymerization Using Methylalumoxane

A 1-liter Zipperclave stainless steel reactor vessel equipped with an inclined blade stirrer, an external jacket for temperature control, a septum inlet and vent line, and a regulated supply of dry ethylene and nitrogen, was cleaned with boiling toluene and dried and deoxygenated with a nitrogen flow. The reactor temperature was adjusted to 80° C., and 400 cc of distilled toluene was added. Two milliliters of the final solution and precipitate from Example 3 was injected by syringe, and the mixture was stirred at 0 psig under nitrogen. A toluene solution (0.10 cc) containing 0.10 mg of dissolved bis(n-butylcyclopentadienyl)zirconium dichloride was injected. Immediately 90 psig of ethylene was admitted and the reactor was stirred and maintained at 80° C. for 5 minutes at a constant pressure of 90 psig. The product was recovered by rapidly venting, cooling, and opening the reactor. Residual toluene was evaporated in a stream of air, and the yield was weighed. The product was determined to be 1.0 g of polyethylene by infrared and gel permeation chromatography. The catalyst activity was calculated to be 44,200 grams polymer per gram zirconium-hour-bar.

What is claimed is:

1. A process for the preparation of a mixture of linear and cyclic hydrocarbylalumoxane which comprises adding a hydrocarbon solution containing trihydrocarbylboroxine to a hydrocarbon solution containing hydrocarbylaluminum and recovering the alumoxane.

2. The process of claim 1, wherein the molar ratio of trihydrocarbylboroxine to hydrocarbylaluminum is about 1:3.05 to about 1:4.

3. The process of claim 1, wherein the hydrocarbylaluminum is trialkylaluminum.

4. The process of claim 3, wherein the trialkylaluminum is trimethylaluminum.

5. The process of claim 1, wherein the hydrocarbon solution is selected from the group consisting of toluene, hexane, and heptane.

6. The process of claim 1, wherein the trihydrocarbylboroxine is trimethylboroxine or triethylboroxine.

* * * * *

UNITED STATES PATENT AND TRADEMARK OFFICE
CERTIFICATE OF CORRECTION

PATENT NO. : 4,952,714
DATED : Aug. 28, 1990
INVENTOR(S) : H. C. Welborn, Jr.

It is certified that error appears in the above-identified patent and that said Letters Patent is hereby corrected as shown below:

Column 3, line 32, delete the formula "$B_2O_3 = R'_3B \rightarrow (R'BO)_3$" and substitute therefor -- $B_2O_3 + R'_3B \rightarrow (R'BO)_3$ --.

Column 3, line 33, delete "$C_1 = = C_{10}$" and substitute therefor -- $C_1$-$C_{10}$ --.

Column 3, line 34, delete "$C_6 = = = C_{10}$" and substitute therefor -- $C_6$-$C_{10}$ --.

Column 3, line 34, delete "$C_1 = = C_{10}$" and substitute therefor -- $C_1$-$C_{10}$ --.

Column 3, line 39 carried over to line 40, delete "$(n+m)(RBO)_3 + 3(n+m+1)R_3Al \rightarrow 3\text{-}(RAlO)_m + 3[R=(R=Al=O)_n=AlR_2] + 3(m+n)R_3B$" and substitute therefor
-- $(n+m)(RBO)_3 + 3(n+m+1) R_3Al \rightarrow 3(RAlO)_m + 3[R\text{-}(R\text{-}Al\text{-}O)_n\text{-}AlR_2] + 3(m+n)R_3B$ --.

Signed and Sealed this

Fifth Day of January, 1993

Attest:

DOUGLAS B. COMER

Attesting Officer

Acting Commissioner of Patents and Trademarks